(12) United States Patent
Chuter et al.

(10) Patent No.: US 10,729,570 B2
(45) Date of Patent: Aug. 4, 2020

(54) MEDICAL BALLOON WITH VARIED COMPLIANCE

(71) Applicant: West Coast Catheter, Inc., San Francisco, CA (US)

(72) Inventors: Timothy A. M. Chuter, San Francisco, CA (US); John Luke Chuter, San Francisco, CA (US)

( * ) Notice: Subject to any disclaimer, the term of this patent is extended or adjusted under 35 U.S.C. 154(b) by 1048 days.

(21) Appl. No.: 14/477,441

(22) Filed: Sep. 4, 2014

(65) Prior Publication Data

US 2015/0081006 A1    Mar. 19, 2015

Related U.S. Application Data

(60) Provisional application No. 61/878,954, filed on Sep. 17, 2013.

(51) Int. Cl.
*A61F 2/958* (2013.01)
*B32B 5/12* (2006.01)
(Continued)

(52) U.S. Cl.
CPC ........... *A61F 2/958* (2013.01); *A61M 25/104* (2013.01); *B32B 5/022* (2013.01); *B32B 5/12* (2013.01);
(Continued)

(58) Field of Classification Search
CPC .............. A61F 2/958; A61F 2230/0013; A61F 2230/001; A61F 2002/826;
(Continued)

(56) References Cited

U.S. PATENT DOCUMENTS 2,472,485 A    6/1949 Krippendorf
5,620,457 A    4/1997 Pinchasik et al.
(Continued)

FOREIGN PATENT DOCUMENTS

EP    0 024 050 A1    2/1981
EP    0 687 189 B1    6/2000
(Continued)

OTHER PUBLICATIONS

Extended European Search Report for European Application No. 13275052.2, dated Aug. 13, 2013, 8 pages.
(Continued)

*Primary Examiner* — Katherine M Shi
*Assistant Examiner* — Michael G Mendoza
(74) *Attorney, Agent, or Firm* — William A. English; Vista IP Law Group LLP (57) ABSTRACT

A medical lumen-expansion balloon may include a generally cylindrical central body between first and second body end portions, a low-profile unexpanded first state and a radially-expanded second state, wherein the first body end portion is constrained by fiber material such that it will not expand longitudinally and circumferentially beyond a predetermined size, and the central body is constrained by fiber material so as to be circumferentially substantially noncompliant, but is longitudinally compliant, such that it will elongate with increased volume but will not substantially radially expand.

17 Claims, 7 Drawing Sheets

(51) Int. Cl.
  *B32B 5/02* (2006.01)
  *B32B 27/12* (2006.01)
  *A61M 25/10* (2013.01)
  *A61F 2/82* (2013.01)

(52) U.S. Cl.
  CPC ........ *B32B 27/12* (2013.01); *A61F 2002/826* (2013.01); *A61F 2002/9583* (2013.01); *A61F 2230/001* (2013.01); *A61F 2230/0013* (2013.01); *A61F 2250/0003* (2013.01); *A61F 2250/0018* (2013.01); *A61F 2250/0028* (2013.01); *A61F 2250/0039* (2013.01); *A61F 2250/0048* (2013.01); *A61M 2025/1059* (2013.01); *A61M 2025/1075* (2013.01); *A61M 2025/1084* (2013.01); *A61M 2205/0216* (2013.01); *B32B 2262/0253* (2013.01); *B32B 2262/0261* (2013.01); *B32B 2535/00* (2013.01)

(58) Field of Classification Search
  CPC .... A61F 2250/0048; A61F 2250/0018; A61M 25/104; B32B 5/022; B32B 27/12; B32B 5/12; B32B 2535/00; B32B 2262/0261; B32B 2262/0253
  See application file for complete search history.

(56) References Cited

U.S. PATENT DOCUMENTS

| | | | |
|---|---|---|---|
| 5,769,817 | A | 6/1998 | Burgmeier et al. |
| 5,868,704 | A | 2/1999 | Campbell et al. |
| 5,876,386 | A | 3/1999 | Samson et al. |
| 6,022,359 | A | 2/2000 | Frantzen |
| 6,187,034 | B1 * | 2/2001 | Frantzen ............ A61F 2/91 623/1.11 |
| 6,206,854 | B1 | 3/2001 | Weaver |
| 6,258,099 | B1 | 7/2001 | Mareiro et al. |
| 6,488,653 | B1 | 12/2002 | Lombardo |
| 6,786,889 | B1 | 9/2004 | Musbach et al. |
| 6,875,197 | B1 | 4/2005 | Simhambhatla et al. |
| 6,923,827 | B2 | 8/2005 | Campbell et al. |
| 7,309,324 | B2 | 12/2007 | Hayes et al. |
| 7,335,184 | B2 | 2/2008 | Laguna |
| 7,635,510 | B2 | 12/2009 | Horn et al. |
| 7,682,335 | B2 * | 3/2010 | Pepper ............ A61L 29/085 604/103.09 |
| 8,002,741 | B2 | 8/2011 | Hayes et al. |
| 8,122,809 | B2 | 2/2012 | Simpson |
| 8,221,351 | B2 | 7/2012 | Pepper et al. |
| 8,292,912 | B2 | 10/2012 | Burton et al. |
| 8,585,959 | B2 | 11/2013 | Burton |
| 2001/0039395 | A1 | 11/2001 | Mareiro et al. |
| 2003/0004535 | A1 | 1/2003 | Musbach et al. |
| 2003/0114915 | A1 | 6/2003 | Mareiro et al. |
| 2004/0082965 | A1 | 4/2004 | Beckham |
| 2005/0049677 | A1 * | 3/2005 | Farnan ............ A61F 2/86 623/1.15 |
| 2006/0030920 | A1 | 2/2006 | Ben-Muvhar |
| 2006/0271091 | A1 | 11/2006 | Campbell et al. |
| 2007/0250101 | A1 | 10/2007 | Horn et al. |
| 2007/0265565 | A1 | 11/2007 | Johnson |
| 2010/0023047 | A1 | 1/2010 | Simpson |
| 2010/0042198 | A1 | 2/2010 | Burton |
| 2010/0179581 | A1 | 7/2010 | Beckham |
| 2010/0234802 | A1 | 9/2010 | Pepper et al. |
| 2010/0243135 | A1 | 9/2010 | Pepper et al. |
| 2011/0022152 | A1 | 1/2011 | Grandt |
| 2011/0172698 | A1 | 7/2011 | Davies, Jr. et al. |
| 2011/0295203 | A1 | 12/2011 | Hayes et al. |
| 2012/0018090 | A1 | 1/2012 | Horn et al. |
| 2012/0022563 | A1 | 1/2012 | Leffel |
| 2012/0277783 | A1 | 11/2012 | Cummins et al. |
| 2013/0123696 | A1 | 5/2013 | Horn et al. |
| 2013/0190796 | A1 | 7/2013 | Tilson et al. |
| 2013/0261546 | A1 | 10/2013 | Aggerholm et al. |

FOREIGN PATENT DOCUMENTS

| | | |
|---|---|---|
| EP | 0 851 777 B1 | 12/2002 |
| JP | 2009-254626 | 11/2009 |
| JP | 2010-115375 | 5/2010 |
| WO | WO 00/57815 A1 | 10/2000 |
| WO | WO 00/57816 A1 | 10/2000 |
| WO | WO 02/068011 A1 | 9/2002 |
| WO | WO 2005/025648 A2 | 3/2005 |
| WO | WO 2005/120622 A3 | 12/2005 |
| WO | WO 2007/123588 A1 | 11/2007 |
| WO | WO 2007/133883 A2 | 11/2007 |
| WO | WO 2008/063782 A2 | 5/2008 |
| WO | WO 2009/080320 A1 | 7/2009 |
| WO | WO 2012/009486 A2 | 1/2012 |

OTHER PUBLICATIONS

International Search Report for International Application No. PCT/US2013/032809, dated Aug. 20, 2013, 4 pages.

Extended European Search Report in corresponding European Application No. 14275193.2, dated Jan. 23, 2015, 6 pages.

\* cited by examiner

MEDICAL BALLOON WITH VARIED COMPLIANCE

CROSS-REFERENCE TO RELATED APPLICATIONS

This application is a non-provisional application which claims priority to U.S. provisional application Ser. No. 61/878,954, filed Sep. 17, 2013, which is incorporated by reference herein in its entirety.

TECHNICAL FIELD

Embodiments disclosed herein generally relate to medical devices. More particularly the present embodiments relate to balloon catheters used to dilate narrowed portions of a lumen and/or to deliver one or more stents into a lumen.

BACKGROUND

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow). Although balloon catheters are used in many other procedures as well, coronary angioplasty using a balloon catheter has drawn particular attention from the medical community because of the growing number of people suffering from heart problems associated with stenosis. This has led to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

One problem that may be encountered with conventional angioplasty devices and techniques is the proper dilation of stenosed regions that are located along a curved section of a lumen, at a junction of a small branch vessel with a significantly larger primary vessel, and/or across branching regions of a vessel. Existing devices may distort or even damage the vessel wall defining the body lumen (e.g., arterial wall). The behavior of an angioplasty balloon is largely dictated by its compliance. A balloon made of low-compliance material(s) generally tolerates high inflation pressures and attains a uniform predictable diameter even when some parts of the surrounding artery contain areas of severe stenosis and dense calcification that resist dilatation. A potential drawback is that a low-compliance balloon always straightens as it expands, regardless of the shape of the surrounding artery. If such a balloon is being used to drive the expansion of a stent, the shape of the balloon, a straight cylinder, is imposed on the shape of the stent. The presence of a straight stent in a curved artery causes stresses and strains that damage either the stent or the artery.

Both effects can lead to arterial microtrauma, hyperplasia and restenosis, especially if the vessel is moving (for example, with the cardiac cycle in the case of a coronary stent, with respiration in the case of a renal stent, or with movement of the thigh and leg in the case of a superficial artery stent). Balloons made of high-compliance materials face a different set of problems which often made them unsuitable for high-pressure angioplasty of unyielding lesions. A compliant balloon expands into whatever low resistance space is available, such as the lumen of the artery upstream and downstream of the lesion and areas of weakness in the arterial wall. High-pressure inflation of a high-compliance balloon may cause potentially damaging inflation of non-diseased segments of the artery, and rupture of a weak segment. Lower pressure inflation leaves many of the more severe lesions untreated. In addition, a high-compliance balloon may fail to provide the force needed to expand a stent in areas of arterial disease, particularly when the diameter is small and higher inflation pressures are required to general sufficient wall tension.

The embodiments described below may be useful in treating stenosed regions along curved vessel regions, along branched vessel regions, and at or near vessel junctions. The claimed embodiments may also solve other problems as well.

It may be desirable to provide a balloon that includes discrete circumferentially-restrained regions, as well as including an ability to provide for longitudinal expansion while not exceeding a predetermined outer diameter.

BRIEF SUMMARY

In one aspect, embodiments disclosed herein may include a medical dilation balloon, as well as methods for same. In a particular aspect, a medical lumen-expansion balloon embodiment may include a generally cylindrical central body between first and second body end portions, a low-profile unexpanded first state and a radially-expanded second state, wherein the first body end portion and second body end portion are substantially non-compliant such that neither will expand further longitudinally and circumferentially, and where the central body is circumferentially substantially noncompliant, but is longitudinally compliant, such that it will elongate with increased volume but will not substantially radially expand.

In another particular aspect, embodiments of a medical lumen-expansion balloon may include a generally cylindrical central body between first and second body end portions, a low-profile unexpanded first state and a radially-expanded second state, wherein the first body end portion is constrained by fiber material such that it will not expand longitudinally and circumferentially beyond a predetermined size, and the central body is constrained by fiber material so as to be circumferentially substantially noncompliant, but is longitudinally compliant, such that it will elongate with increased volume but will not substantially radially expand.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

The terms "proximal" and "distal" are used herein in the common usage sense where they refer respectively to a handle/doctor-end of a device or related object and a tool/patient-end of a device or related object.

Figures 1, 2, 3:
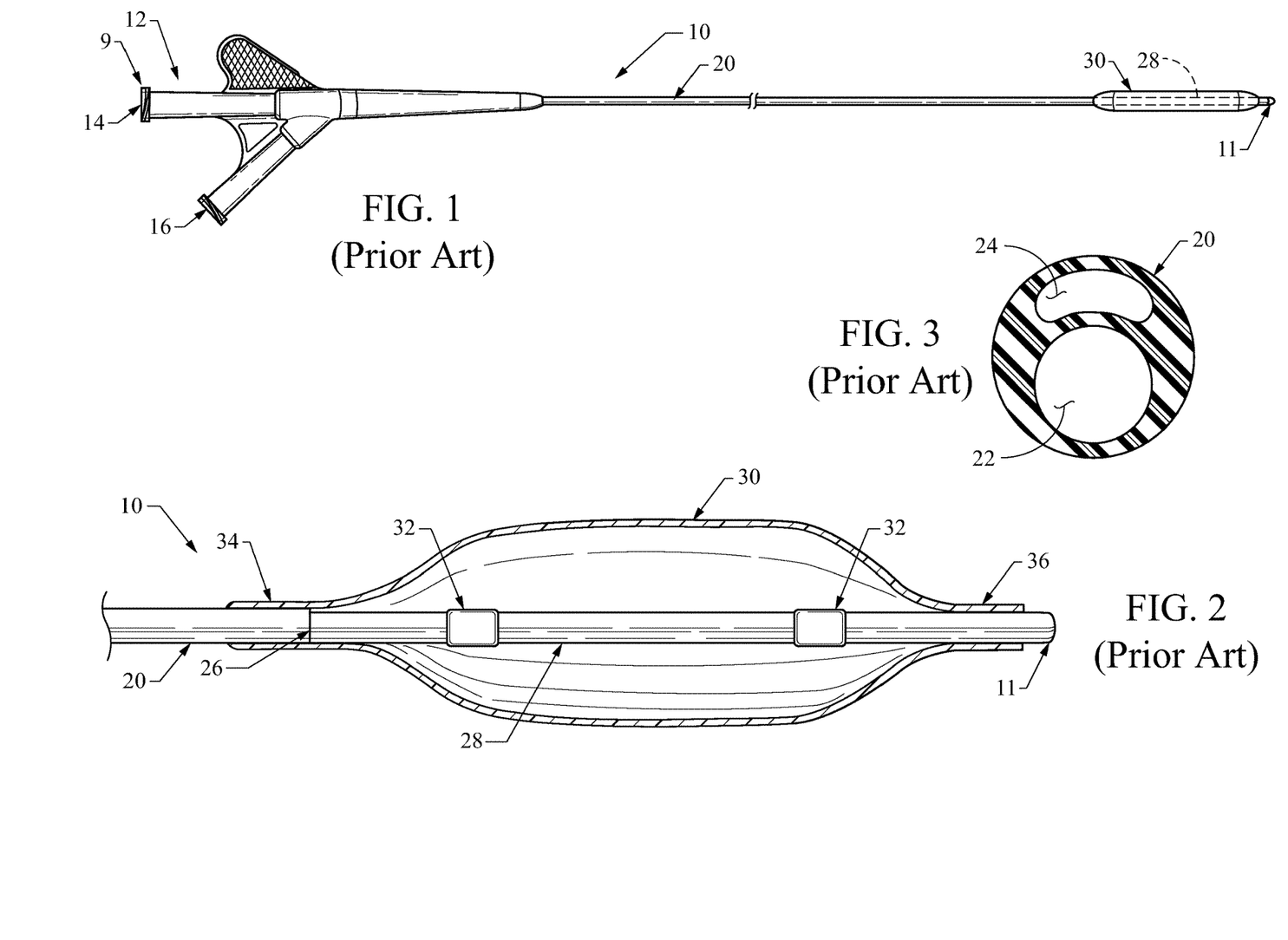
FIGS. 1-3 show, respectively, external, distal longitudinal section, and transverse section views of a typical balloon catheter.

Referring now to FIGS. 1-3, a prior art balloon catheter 10 is shown. Typically, a balloon catheter 10 includes a manifold 12 near the proximal end 9 of the catheter 10 with one or more ports 14, 16. For example, the balloon catheter 10 that is shown has one port 14 for a wire guide 18 and one port 16 for inflation media. The manifold 12 is attached to a proximal shaft 20 that extends toward the distal end 11 of the catheter 10. As shown in FIG. 3, the proximal shaft 20 may have two different lumens 22, 24 passing longitudinally through the proximal shaft 20. In the example shown, one lumen 22 is for the wire guide 18 and the other lumen 24 is for the inflation media. Thus, the wire guide port 14 of the manifold 12 opens to the wire guide lumen 22, and the inflation port 16 opens to the inflation lumen 24. The described manifold, ports and lumens, however, are only one example of the type of structure that may be used with a balloon catheter and many other examples are possible as well.

At the distal end 26 of the proximal shaft 20, the proximal shaft 20 may be bonded to an inner shaft 28. As used herein, the term "bonded" simply refers to the boundary between two portions and is not meant to refer to a particular technique for adhering two members together. For example, two shafts may be bonded together by gluing, heat welding, friction welding or the like. However, shafts may also be bonded together by extruding a shaft with two different portions having different shapes, material properties or other characteristics. Furthermore, two members may be attached in various other ways, including with intermediate members disposed therebetween. As shown in FIG. 2, the inner shaft 28 is smaller in diameter than the proximal shaft 20 and is shifted from the center axis of the proximal shaft 20 so that the wire guide lumen 22 of the proximal shaft 20 lines up with a matching wire guide lumen 22 extending through the inner shaft 28. Because the inner shaft 28 is smaller in diameter than the proximal shaft 20 and is shifted away from the inflation lumen 24, the inflation lumen 24 is exposed at the distal end 26 of the proximal shaft 20 to the interior of the balloon 30.

In the prior art embodiment shown in FIGS. 1-3, the inner shaft 28 extends to the distal end 11 of the catheter 10. Radiopaque bands 32 may be added to the inner shaft 28 to allow the physician to see the location of the balloon catheter 10 with visualization equipment during intraluminal procedures. The wire guide lumen 22 of the catheter 10 opens at the distal end 11 of the catheter 10 to allow the catheter 10 to pass over a wire guide 18. The inner shaft 28 is encompassed by a balloon 30, which may be used in angioplasty procedures or various other procedures. As shown, the proximal end 34 of the balloon 30 is bonded to both the proximal shaft 20 and the inner shaft 28. However, the proximal end 34 could be bonded to only the proximal shaft 20 or the inner shaft 28 as desired. The distal end 36 of the balloon 30 is bonded to the inner shaft 28. Although various materials may be used for the balloon catheter 10, nylon-based materials, such as polyether block amide (PEBA), which are biocompatible, may be used for most of the components.

Figure 4:
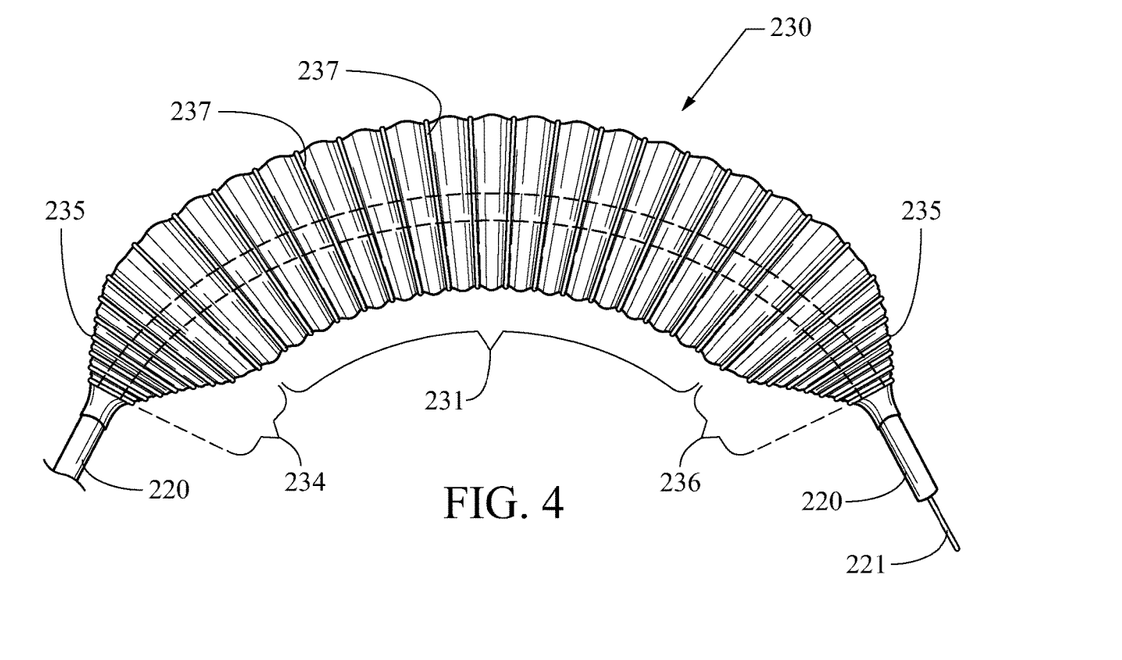
FIGS. 4 and 4A show, respectively, a side view and a detail side view of a medical balloon embodiment including radially/circumferentially restraining fiber material.
Figure 4A:
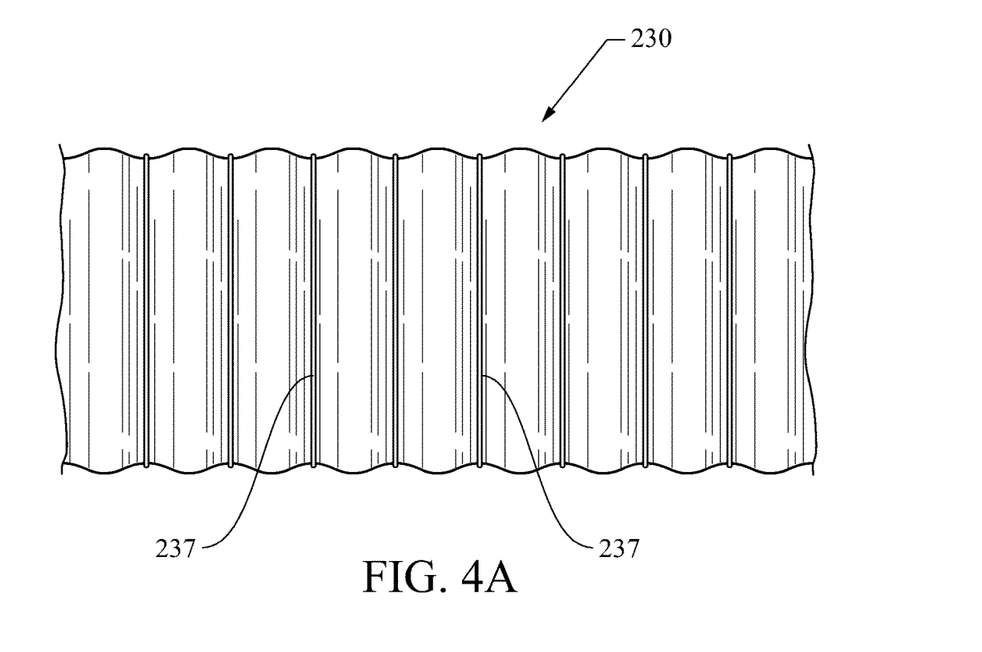

One embodiment of a medical balloon 230 with varied compliance is described with reference to FIG. 4, which shows a side view of the balloon 230 as it may be disposed within a curved artery. This embodiment provides one solution to the problems associated with high-pressure balloons addressed in the background section above. It provides a balloon 230 with high-compliance in one dimension (along the length of the balloon) and a low-compliance in the other dimension (around the circumference of the balloon). Constraining fiber(s) are provided around the circumference of the balloon, thereby restricting its radial/transverse expansion. Longitudinal fibers, if any, may be loose at full balloon expansion and/or may be elastic such that they generally do not limit lengthening of the balloon. The constraining fibers do not need to cover the entire surface of the balloon; rather, they can be separated by short gaps. The balloon material may bulge between adjacent constraining fibers, but preferably not enough to produce a significant increase in balloon diameter, as shown in FIGS. 4-4A, described below. In other aspects, the balloon may be configured with a balloon catheter as shown in FIGS. 1-3, or any other balloon catheter configuration known in the art or developed in the future.

The balloon 230 includes a generally cylindrical central body 231 between a first body end portion 234 and a second body end portion 236. As is well-known in the balloon art, the balloon 230 is deployed via a balloon catheter 220, which may be directed along a wire guide 221, and includes a low-profile unexpanded first state (not shown) and a radially-expanded second state (shown in FIG. 4). In this radially-expanded state, first body end portion 234 and a second body end portion 236 are reinforced with constraining fiber 235, configured (e.g., wound, attached, or otherwise expansion-limiting) such that one or both are substantially non-compliant ("substantially non-compliant" meaning that the constraint is such that it/they will not expand further longitudinally or circumferentially under normal operating conditions).

The central body 231 is circumferentially substantially noncompliant, but is longitudinally compliant, such that it will elongate with increased volume of the lumen defined by the body 231 but will not substantially radially expand. This compliance profile is provided by inclusion of substantially inelastic circumferentially-constraining fiber 237. The circumferentially-constraining fiber 237 may be embodied as a single thread/yarn-like fiber or a plurality of such that are continuous, connected, or unconnected. This fiber 237 may be continuous with or separate from the constraining fiber 235 of the body end portion(s). The fiber may be any biocompatible textile or composite thereof, preferably substantially inelastic with limited tensile stretchability sufficient to provide the substantial non-compliance described herein. Specific fiber materials may include UHMW (ultra-high-molecular weight) polymers, nylon, polyethylene, or other suitable materials known or developed. The fiber 237 may be disposed on, within, and/or on an inner surface of the balloon 230. It may be configured as a series of connected or unconnected loops, one or more helices, or any other configuration or combination of configurations along the length of the central body 231 that provide substantial radial non-compliance beyond an inflated outer diameter, but that provide (in conjunction with the balloon material) longitudinal compliance allowing the balloon to expand longitudinally with continued inflation after it has ceased expanding radially.

The balloon body construction preferably is of an elastomeric polymer. As shown in FIG. 4, and in the detail view of FIG. 4A, the elastomeric construction of the balloon's wall may allow it to bulge slightly between longitudinally adjacent dispositions of the radially-constraining fiber 237 (although it should be appreciated that the bulge may be very slight in certain, such that the drawing figure bulges may be considered as exaggerated and not to scale). This feature may be useful if the balloon 230 is used for deployment of one or more stents, as the "inter-bulge spaces" may provide a generally ribbed outer surface contour as a means for maintaining longitudinal relative position of a stent during deployment, as is described below. In particular, this balloon configuration (and other configurations described herein) may be useful for reducing the possibility that an unexpanded stent may move longitudinally along a balloon's surface as the slightly irregular surface may provide retention functionality.

Figure 5:
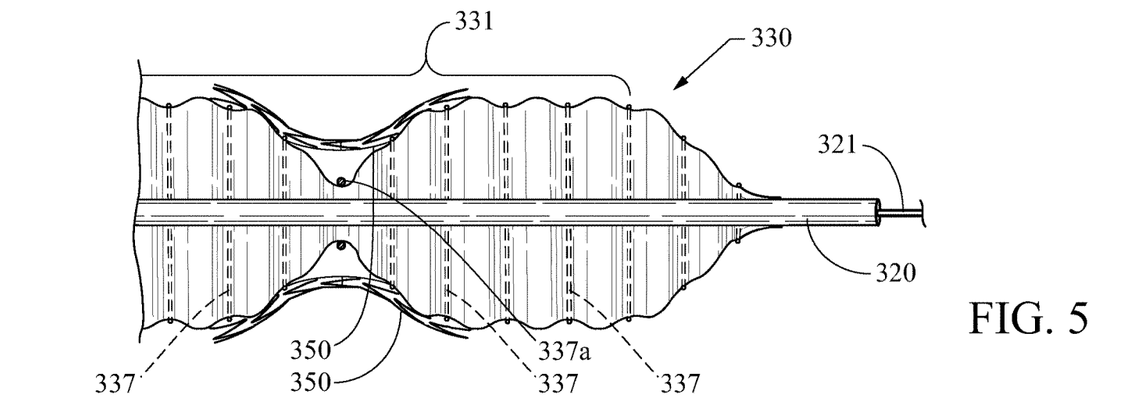
FIGS. 5 and 5A show, respectively, distal longitudinal section views of a partially-inflated and fully-inflated medical balloon embodiment including radially/circumferentially restraining fiber material, deploying stents.
Figure 5A:
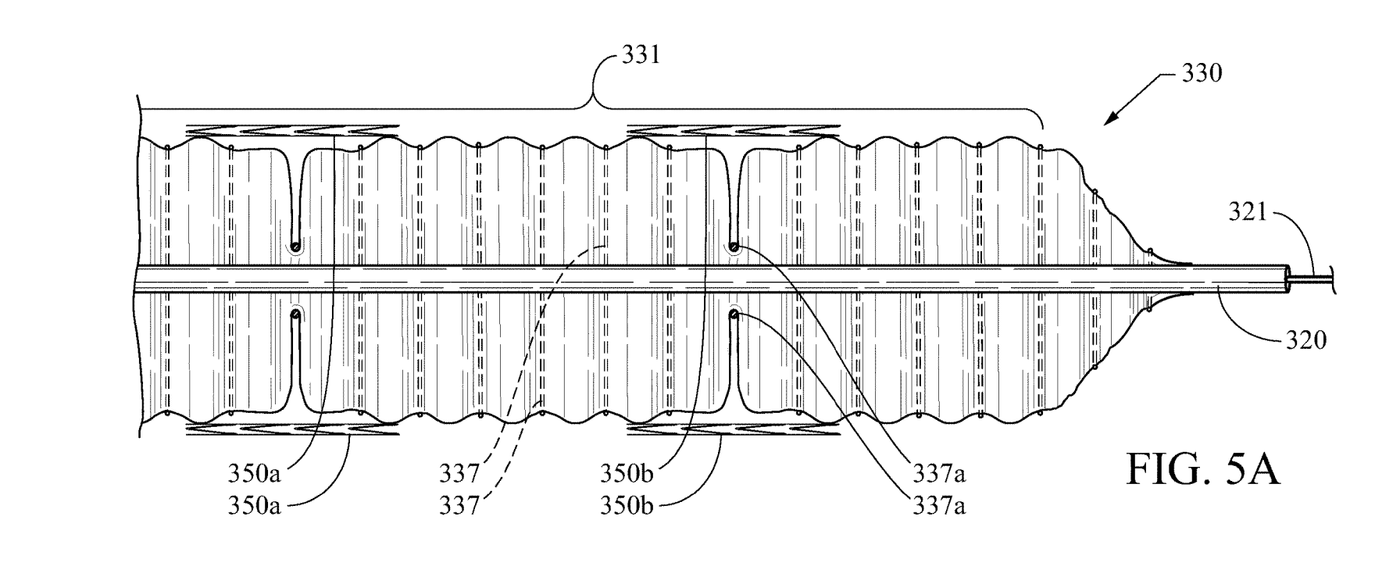

FIGS. 5-5A each show a diagrammatic longitudinal section view of an embodiment of a balloon 330 constructed for stent-deployment, in partially-expanded and fully-expanded configurations, respectively. The general construction is generally similar to that of the embodiment of FIGS. 4-4A, including an elastomeric central body 331 that is radially constrained by fiber(s) 337. In this embodiment certain of the radial-constraining fiber 337 is configured with a diameter that is much smaller than the expanded radial diameter of the balloon 330. The fiber 337 loop or helical portion defining these smaller-diameter regions is designated in FIGS. 5-5A by reference number 337a. The balloon 330 may be constructed for introduction with a balloon catheter 320 directed along a wire guide 321.

For treating certain conditions and/or to establish and/or maintain an open patent lumen, it may be useful to deploy a plurality of shorter-length stents than a single longer stent. FIG. 5A shows a plurality of shorter-length balloon-deployable stents 350 (as 350a, 350b). Each of the stents 350 is generally longitudinally centered over a smaller-diameter radially-constraining fiber portion 337a. As shown in FIG. 5, this will help to longitudinally position a stent 350 in a manner that generally prevents it from moving longitudinally during deployment. Such a configuration will provide for accurate positioning and deployment of a stent using standard fluoroscopic and/or ultrasound visualization techniques. The smaller-diameter-permitting constraining fiber portion 337a may be continuous with, connected to, or unconnected from the larger-diameter-permitting radially constraining fiber 337.

In some stent and balloon configurations it is possible that the converging balloon surfaces on either side of a constraining (small) suture might partially capture and squeeze a stent causing it to flare from a central, incompletely expanded center. One way to avoid this problem may be to effect the release of the smaller-diameter-permitting radial-constraints (e.g., early in stent expansion). With such a device and method, the stent will still be held in place by a "more-constrained valley" in the balloon surface, but forced to expand when the "floor of the valley" rises after removal of the smaller constraint. In one embodiment, shown in FIGS. 6A-6C, the smaller-diameter-permitting radial-constraints 437a comprise loops 437a (e.g., of suture material or other biocompatible material) that are wrapped around the central body 431 of the balloon 430 and held in place by a trigger wire 460. The trigger wire 460 passes through one or both ends of each loop 437a. In some embodiments, one end of each loop 437a may be attached to a continuous fiber 437 and another end, but for the presence of the trigger wire, is unattached.

Figure 6A:
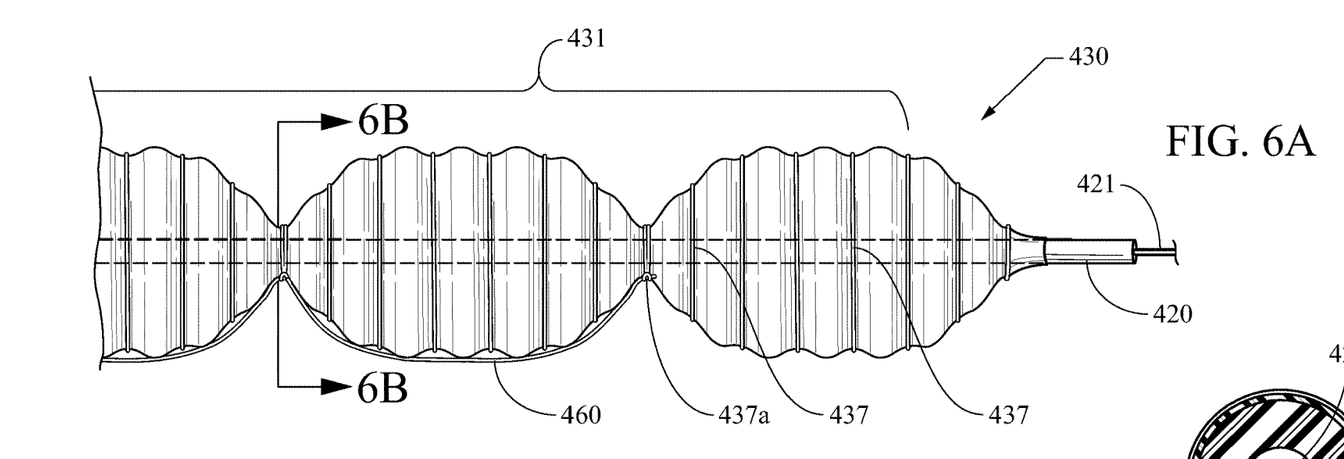
FIG. 6A shows a distal portion side view of a medical balloon embodiment including radially/circumferentially restraining fiber material, with smaller-diameter, releasable restraints.
Figures 6B, 6C:
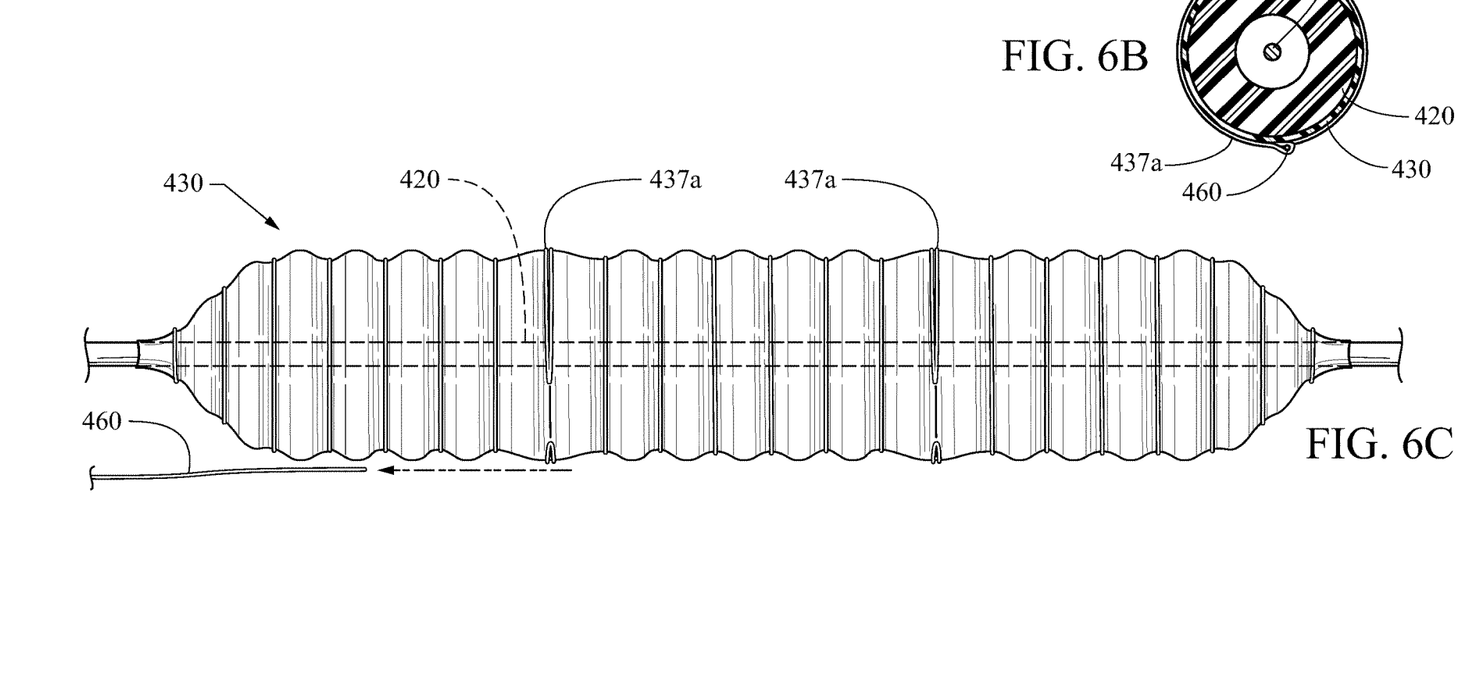
FIG. 6B shows a transverse section view taken along line 6B-6B of FIG. 6A.
FIG. 6C shows release of radially-constraining fiber portions by retraction of a trigger wire.

FIG. 6A shows the balloon 430 only partially inflated, with the trigger wire 460 engaged with the loops 437a. FIG. 6B shows a transverse section, taken along line 6B-6B, which shows the concentric arrangement of the loops 437a, balloon wall 430, balloon catheter 420, and wire guide 421. It also shows where the trigger wire 460 or analogous wire-attached structure is engaged through the loop 437a. For clarity of illustration stents are not shown overlying the loops 437a, but those of skill in the art will appreciate the structure and function disclosed regarding stent deployment with reference to FIGS. 5-5A. Specifically, the configuration of the balloon 430 in FIG. 6 is directly analogous to the configuration shown in FIG. 5, where the smaller-diameter radially-constraining fiber portions 337a are generally centered beneath a stent. Then, FIG. 6C shows how the smaller-diameter radially-constraining fiber portions may be released in this embodiment to allow the central balloon body 431 to assume a generally uniform outer diameter in contrast with the periodically-constrained configuration shown in FIG. 5A. A phantom arrow indicates retraction of the trigger wire 460 out of the loops.

In particular, FIG. 6C shows the trigger wire 460 having been withdrawn from the loops 437a. This releases the loops 437a, such that they no longer substantially constrain any portion of the balloon body circumference. In view of the present disclosure, those of skill in the art will appreciate that, in some embodiments, the trigger wire 460 need not be retracted from the loops 437a. Rather, in certain embodiments, the portion of the trigger wire 460 that contacts and restrains the loops 437a (or a trigger-wire-connected structure such as suture material that is functionally the same as or at least continuous with the illustrated trigger wire) may be flexible and just held in tension sufficient to restrain the loops 437a in the smaller-radius configuration. For such an embodiment, releasing the tension will allow that contacting/restraining portion to sinuously flex, thereby releasing the loops 437a to a more open/larger radius configuration.

As noted above, it is preferred that the balloon embodiments disclosed here are circumferentially fiber-constrained at a specifically predetermined outer diameter (which will be constructed in keeping with the intended use of a given balloon: e.g., very small for peripheral or other small blood vessels, but larger for use in a primary artery, or significantly larger for use in a gastrointestinal or urinary-tract lumen). However, the balloon embodiments preferably allow continued longitudinal expansion within the mechanical limits of the elastomeric balloon body material. The proximal-end and distal-end portions of the balloon will be both circumferentially and longitudinally constrained to provide a predictable and useful shape profile. In view of the present disclosure, those of skill in the art of textile-reinforced balloons will appreciate that this configuration may be accomplished in several manners, some of which are now described with reference to FIGS. 7-9.

Figure 7:
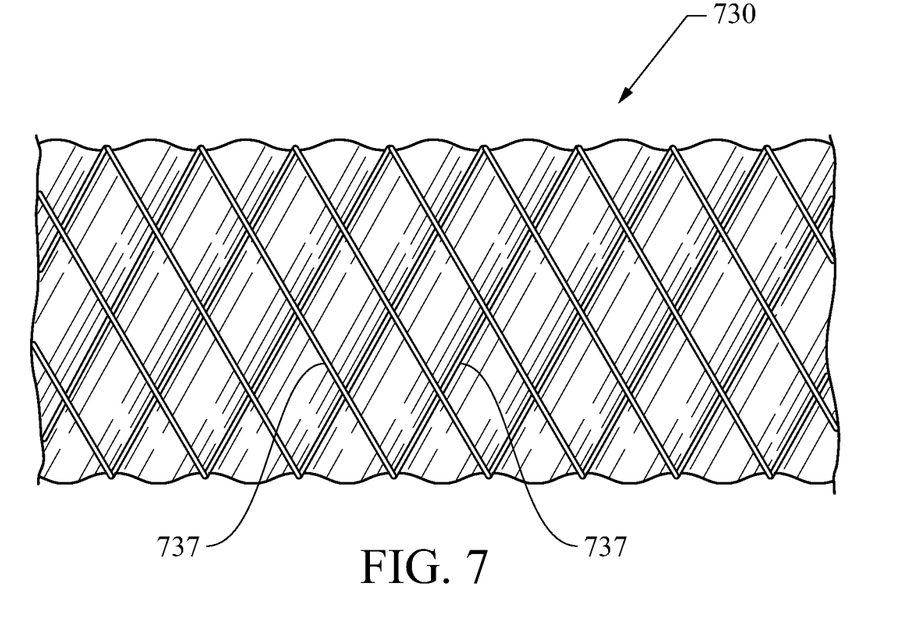
FIG. 7 illustrates an embodiment of a radially/circumferentially restraining fiber material braid pattern along a central, generally cylindrical balloon body portion.

FIG. 7 shows a central body portion of a balloon 730 surrounded by radial-constraint fibers 737. The fibers 737 are shown as braided with a wide braid angle, but—in other embodiments—the fibers 737 may be configured as overlapping but non-interwoven counter-helices, or they may be woven in any textile form consistent with radial constraint and longitudinal flexibility. Along the central balloon body length shown, the fibers 737 preferably are not attached to the balloon surface, such that the relative fiber angles can change to accommodate the expansion described. Those of skill in the art will appreciate that this configuration will, during balloon-inflation, provide a maximal radial constraint while simultaneously allowing longitudinal expansion consistent with the principles described above.

Figure 8:
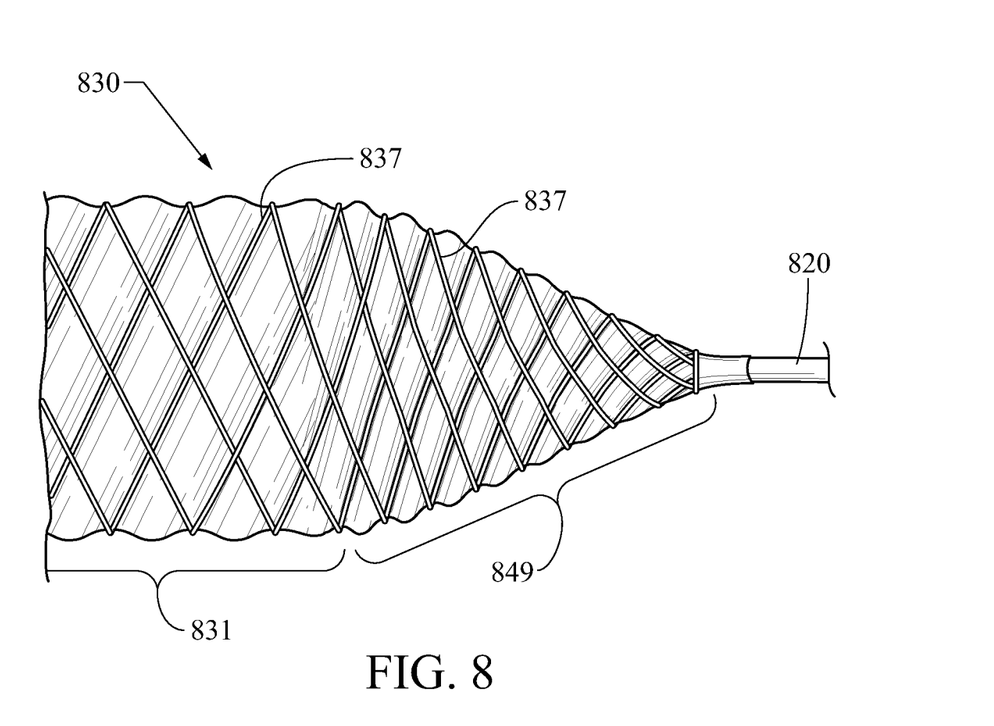
FIG. 8 shows an embodiment of a radially/circumferentially restraining fiber material braid pattern along a central, generally cylindrical balloon body portion, transitioning to a different braid pattern or angle along an end portion that is both radially/circumferentially and longitudinally constrained.

FIG. 8 shows an end portion 849 of a balloon 830, as one possible configuration of a balloon end portion that is both circumferentially and longitudinally constrained by braided fibers 837. The fibers 837 nearest the end attached to a balloon catheter body 820 include a very tight braid angle and may be secured to (or even disposed within) the wall of the balloon 830. Along the balloon length progressing toward the balloon's center, the braid angle widens, and may broaden out along the generally cylindrical central body length 831—for example—to that shown in FIG. 7. As in FIG. 7, the fibers 837 do not need to be interwoven in a braid, but may be configured as overlapping but non-interwoven counter-helices, or they may be woven in any textile form consistent with radial constraint and longitudinal flexibility. Depending upon the manner in which the balloon's elastomeric body is molded; the braid angles, weaving pattern, or other pattern of fiber(s) are changed; and the manner of fiber-to-body attachments (if any), the end portion may be generally conical, domed, or some other generally to substantially tapering shape that decreases in outer diameter from the central body 831 toward the attachment with the balloon catheter 820.

Figure 9:
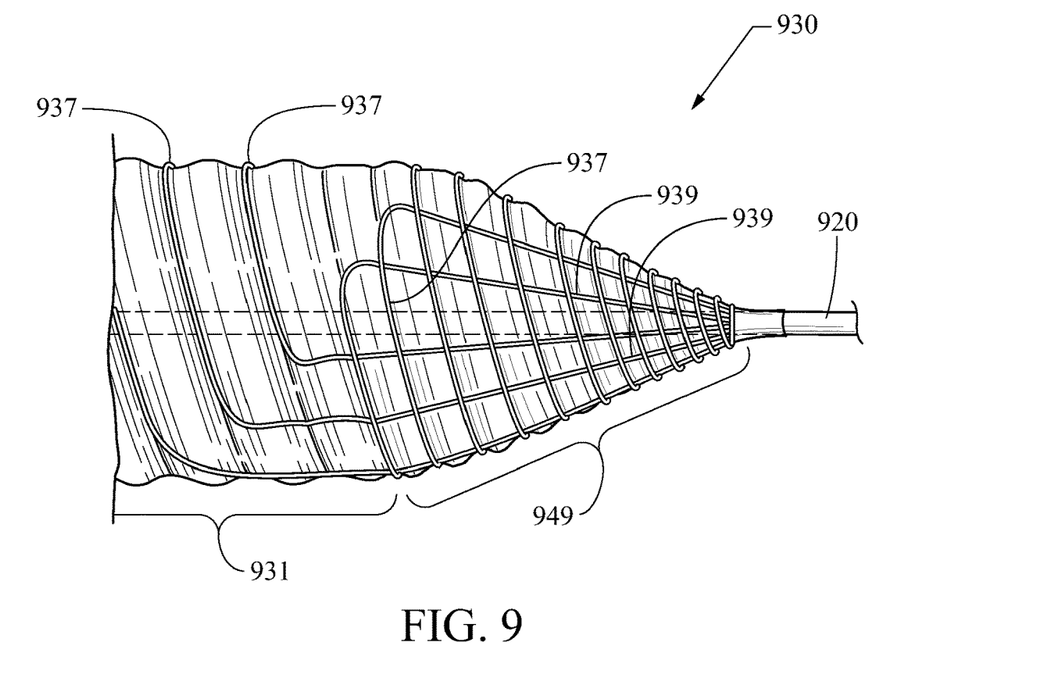
FIG. 9 shows another embodiment of a radially/circumferentially restraining fiber material pattern along a central, generally cylindrical balloon body portion, transitioning to a different pattern an end portion that is both radially/circumferentially and longitudinally constrained.

Another embodiment is illustrated in FIG. 9, which shows a radially-constrained balloon 930. The central balloon portion 931 is radially constrained by a helically wound fiber 937 not attached along that central generally columnar length. The generally conical end portion 949 is both radially and longitudinally constrained as it nears the balloon catheter body 920. Along/around the end portion 949, the pitch of helically-wound fiber 937 is shallower and tighter, and a plurality of longitudinal fibers 939 is provided. Along the end portion 949, the helical and longitudinal fibers 937, 939 may be distinct, continuous with each other, and/or attached to each other, and may be attached onto, within, or into the balloon body. Those of skill in the art will appreciate that this configuration will provide radial/circumferential constraint while permitting balloon elongation as the helical fiber 937 will change pitch to allow said elongation while maintaining radial constraint.

Figure 10:
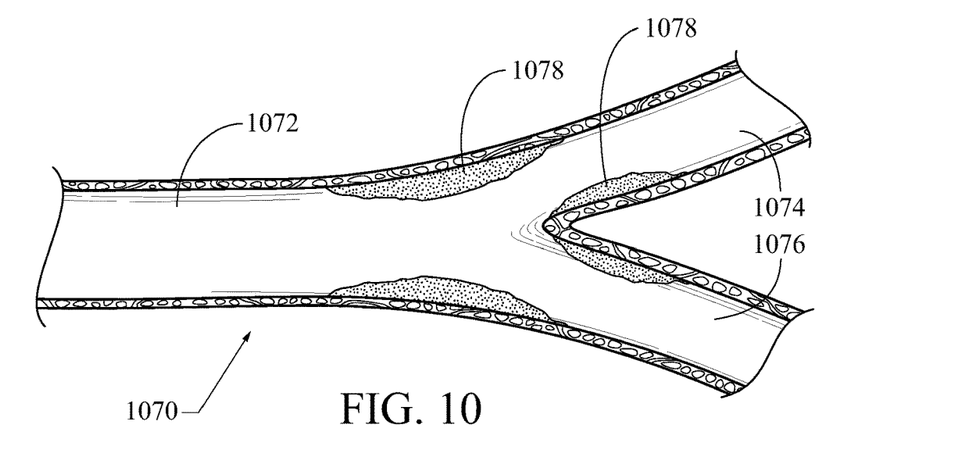
FIG. 10 shows a branched vessel with stenoses.
Figure 10A:
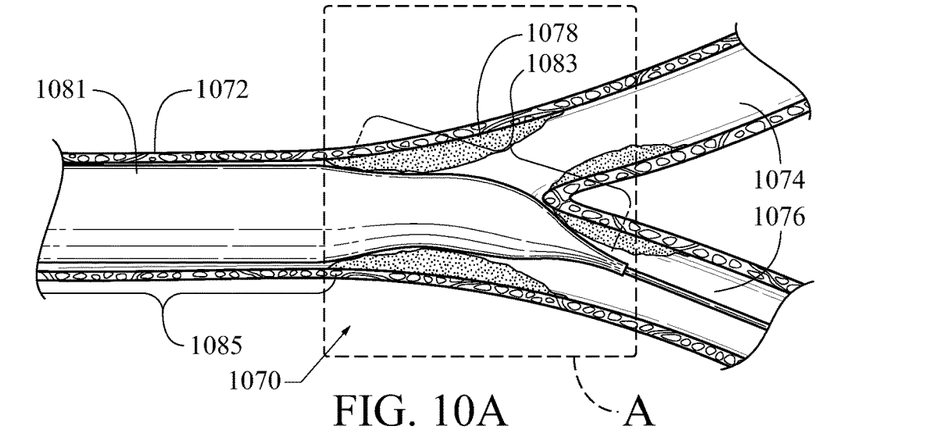
FIG. 10A shows the same vessel as FIG. 10, occupied by a traditional balloon.
Figure 10B:
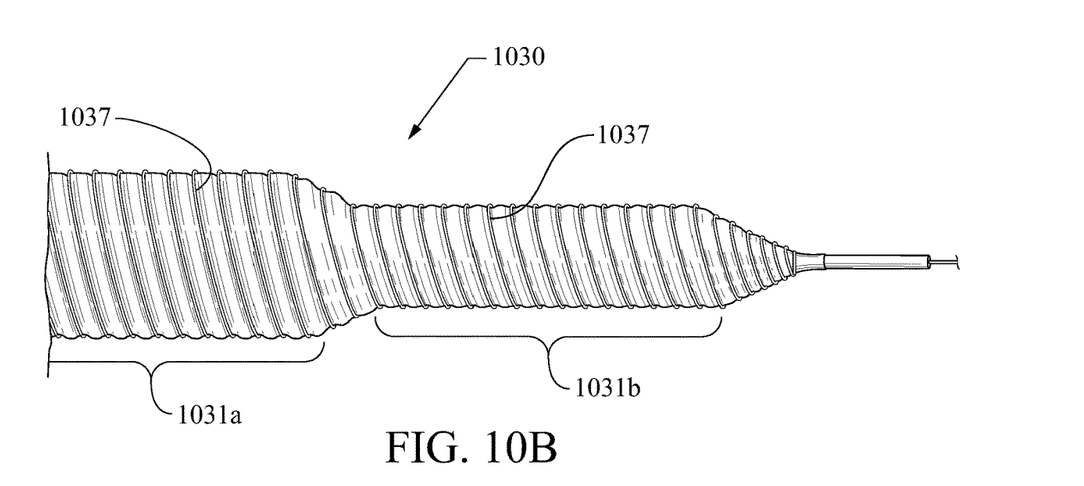
FIG. 10B shows balloon with a plurality of distinct radially/circumferentially fiber-constrained generally cylindrical portions.

Balloon embodiments described herein may be particularly helpful in applications relating to branched vessel locations, including bifurcated vessels with near-bifurcation stenosis and side-branches of much larger vessels (e.g., renal ostium). Use of presently-described embodiments to address these is set forth below with reference to FIGS. 10-11. FIGS. 10-10B show, respectively, a typical bifurcation stenosis, a typical prior art balloon with a generally conical end portion, and a novel balloon embodiment with a stepped-down diameter configured in keeping with the constraining fiber embodiments disclosed herein.

A typical bifurcation stenosis of a blood vessel 1070 is shown in FIG. 10. A main vessel 1072 bifurcates into two smaller vessels 1074, 1076 (e.g., having an inner diameter of about three-fourths or less that of the main vessel), and stenotic deposits 1078 are shown occupying the lumen of the vessels at the bifurcation. As shown in FIG. 10A, a typical dilatation balloon 1081 includes a generally conical end portion 1083 and a generally cylindrical body portion 1085 along a balloon catheter 1087. The balloon 1085 is shown less than fully inflated. In order to dilate the main stenosis, the balloon 1081 must extend at least slightly into one of the smaller branches 1074, 1076. This creates potential risk for the balloon's central body 1085, end portion 1083, and the transition region therebetween to place stress on or near an already-compromised vessel region (particularly in the regions identified by "Box A") when the balloon is fully inflated such that its outer diameter is sufficiently large to dilate the primary stenosis 1078 but is also larger than the inner diameter of the branch vessels 1074, 1076.

Accordingly, FIG. 10B illustrates a balloon embodiment 1030 that has a first, larger-diameter radially/circumferentially-constrained central body portion 1031a and second, smaller-diameter radially/circumferentially-constrained central body portion 1031b. Those radially/circumferentially-constrained central body portions 1031a, 1031b may be constructed like the radially/circumferentially-constrained central body portions of embodiments described above with reference to FIGS. 7-9. Specifically, one or more radially/circumferentially-constraining fibers 1037 are provided around the balloon body to limit its expansion to a predetermined maximal outer diameter. The radially/circumferentially-constrained first central body portion 1031a is wound with the fiber to provide a larger outer diameter than the radially/circumferentially-constrained second central body portion 1031b. The difference between them preferably occurs in a stepped manner (which may include for purposes of the present embodiments a steeply tapered transition). The fiber constraint 1037 may be woven, coiled, braided, or otherwise configured in an interspersed/interwoven, or non-interwoven manner suitable to allow longitudinal expansion while substantially limiting radial expansion to a predetermined maximal outer diameter.

The radially/circumferentially-constrained second central body portion 1031b may be coaxial with and generally centered relative to the radially/circumferentially-constrained first central body portion 1031a, or it may be off-axis/off-center. The radially/circumferentially-constrained second central body portion 1031b may be constructed to align longitudinally/linearly with the radially/circumferentially-constrained first central body portion 1031a, or it may be constructed to assume an off-axis angle. In such an embodiment, it will be most preferable to provide indicia of the direction of extension/angle of the radially/circumferentially-constrained second central body portion 1031b (e.g., proximal indicia on a manipulation handle and/or radio-opaque indicia on the balloon or elsewhere on the device sufficient to provide rotational orientation data to a physician/user). Those of skill in the art will appreciate how deployment of this embodiment in bifurcation stenoses (see, e.g., FIGS. 10-10A) may provide superior targeting of those stenoses as compared to prior balloons.

Figure 11:
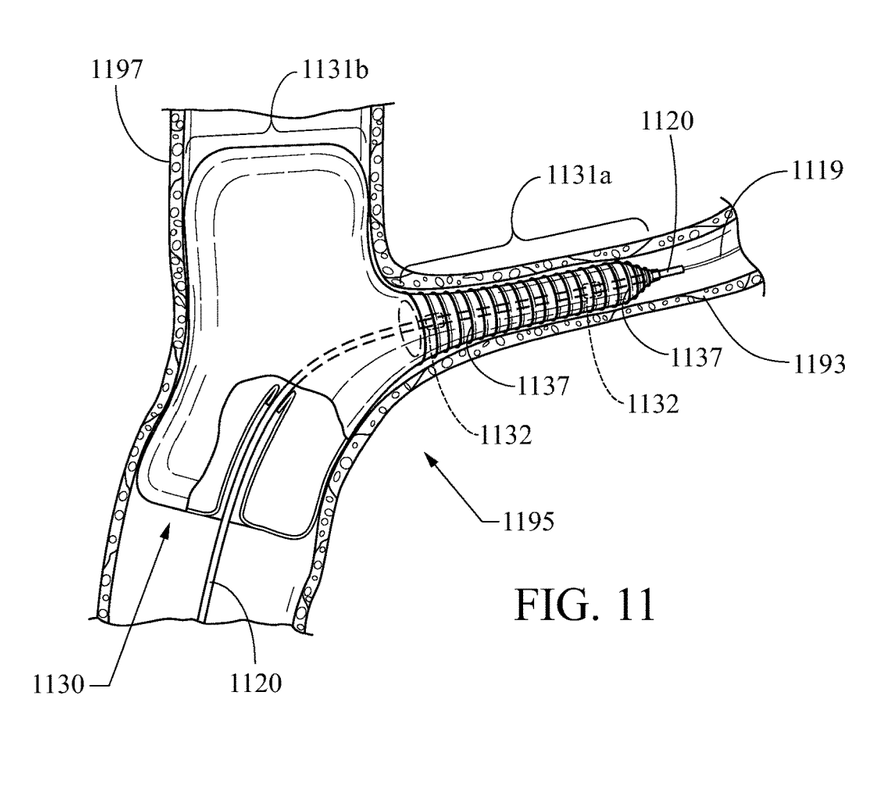
FIG. 11 depicts a renal ostium occupied by a balloon embodiment that has a radially/circumferentially restraining fiber material braid pattern along a generally cylindrical balloon body portion, transitioning from an elastomeric balloon portion that is not so constrained.

FIG. 11 shows another embodiment of a balloon 1130, which includes a fiber-restrained portion that is significantly smaller in diameter than an unconstrained portion. For example, the constrained portion may have ⅓ or less the outer diameter of the unconstrained portion. In this embodiment, a compliant-body balloon is provided with a radially/circumferentially-constrained portion 1131a constrained by one or more fibers 1137 and an unconstrained portion 1131b limited in size and shape by the mechanical configuration of its elastomeric/compliant body composition. The balloon 1130 is mounted on a balloon catheter 1120 that may be directed along a wire guide 1119 to a target region. In FIG. 11, a sample target region is illustrated as a renal ostium 1195, where a renal artery 1193 branches off from the descending aorta 1197. This location is prone to stenosis in certain patients, and presents challenges for angioplasty and stenting that those of skill in the art will appreciate (from the state of the art, and from the description above referring to FIG. 10).

The balloon 1130 therefore provides the radially/circumferentially-constrained portion 1131a to occupy and dilate a stenosis of the small-diameter branch vessel 1193, while the larger balloon portion 1130b can occupy and serve as positional aid and/or anchor in the larger-diameter primary vessel 1197. This construction will allow a user to bring desirable force to bear upon the renal artery stenosis, while the fiber-constrained outer diameter of the balloon portion 1130a occupying that smaller vessel reduces the risk of overdilation or other injury. Radio-opaque markers 1132 may be used for fluoroscopic visualization/identification of the constrained balloon portion 1131a. The constrained portion 1131a may be constructed in keeping with the above-disclosed embodiments, including that it may have a further-reduced diameter portion (not shown).

In each of the foregoing embodiments, expanded outer diameters may range from about 2 mm to about 25 mm and expanded lengths may range from about about 15 mm to about 250 mm, although other embodiments may have other dimensional ranges. In preferred embodiments, the central longitudinally-compliant (but circumferentially-constrained) portion will include at least one half of the total balloon length.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:
1. A medical lumen-expansion balloon comprising:
   a generally cylindrical central body defining a length between first and second body end portions that transition from the central body to ends of the balloon;

a low-profile unexpanded first state;
a radially-expanded second state wherein the central body defines an outer inflated diameter, wherein
the first body end portion and second body end portion taper from the central body to the respective ends of the balloon and are substantially non-compliant such that neither the first body end portion nor the second body end portion will expand longitudinally and circumferentially once the central body is inflated to the outer inflated diameter, and
the central body comprises a plurality of circumferentially-constraining fibers extending circumferentially around the central body and spaced apart from one another along the length such the central body is circumferentially substantially noncompliant, but is longitudinally compliant, the circumferentially-constraining fibers configured to allow the central body to elongate with increased volume but not substantially radially expand beyond the outer inflated diameter, and at least one smaller diameter circumferential constraint fiber surrounding the central body having a smaller diameter than adjacent circumferential-constraining fibers when the central body is inflated to the outer inflated diameter.

2. The balloon of claim 1, further comprising a plurality of balloon-deployable stents disposed around the central body over the circumferential-constraining fibers, ends of adjacent stents spaced apart from one another that are deployable from the balloon for deployment in a lumen of a patient.

3. The balloon of claim 2, where the at least one smaller diameter circumferential constraint fiber is disposed between one of the stents and an outer surface of the balloon, longitudinally central relative to the stent, such that the at least one smaller diameter circumferential constraint fiber restricts radial expansion of the central body under the stent to prevent longitudinal movement of the stent during deployment.

4. The balloon of claim 3, where at least one smaller diameter circumferential constraint fiber is provided under each of the plurality of stents to prevent longitudinal movement of the stents during deployment.

5. The balloon of claim 1, wherein the first body end portion and the second body end portion are reinforced with constraining fibers configured to prevent the first body end portion and the second body end portion from expanding longitudinally and circumferentially once the central body is inflated to the outer inflated diameter.

6. The balloon of claim 1, wherein the one or more circumferentially-constraining fibers are wound around or attached to the central body.

7. The balloon of claim 1, wherein the one or more circumferentially-constraining fibers define loops extending circumferentially around the central body and separated by gaps along the length.

8. The balloon of claim 7, wherein one or more of the loops are configured to expand to a constraining diameter smaller than the outer inflated diameter such that the one or more loops create one or more smaller diameter regions when the central body is inflated to the second state.

9. The balloon of claim 1, further comprising longitudinal fibers extending along the central body that remain loose when the central body is inflated to the outer inflated diameter such that the longitudinal fibers do not limit lengthening of the central body upon further inflation.

10. The balloon of claim 1, wherein the central body comprises elastomeric material, and wherein the one or more circumferentially-constraining fibers are spaced apart to allow the elastomeric material to bulge between longitudinally adjacent fiber regions to provide a ribbed outer surface contour.

11. A medical lumen-expansion balloon comprising:
a generally cylindrical central body having a length between first and second body end portions that transition from the central body to ends of the balloon;
a low-profile unexpanded first state;
a radially-expanded second state wherein the central body defines an outer inflated diameter, wherein
the first body end portion tapers from the central body to a first of the ends of the balloon and is constrained by fiber material such that the first body portion will not expand longitudinally and circumferentially beyond a predetermined tapered size, and
the central body is constrained by a plurality of circumferentially-constraining fibers extending circumferentially around the central body and spaced apart from one another along the length so as to be circumferentially substantially noncompliant, but is longitudinally compliant, such that the central body will elongate with increased volume but will not substantially radially expand beyond the outer inflated diameter, and at least one smaller diameter circumferential constraint fiber surrounding the central body having a smaller diameter than adjacent circumferential-constraining fibers when the central body is inflated to the outer inflated diameter.

12. The balloon of claim 11, where the central body portion includes a first circumferentially fiber-constrained length with a different maximal outer diameter than a second circumferentially fiber-constrained length.

13. The balloon of claim 11, wherein the second body end portion tapers from the central body to a second of the ends of the balloon and is constrained by fiber material such that the second body portion will not expand longitudinally and circumferentially beyond a predetermined tapered size.

14. The balloon of claim 11, wherein the one or more circumferentially-constraining fibers define loops extending circumferentially around the central body and separated by gaps along the length.

15. The balloon of claim 14, wherein one or more of the loops are configured to expand to a constraining diameter smaller than the outer inflated diameter such that the one or more loops create one or more smaller diameter regions when the central body is inflated to the second state.

16. The balloon of claim 11, wherein the central body comprises elastomeric material, and wherein the one or more circumferentially-constraining fibers are spaced apart to allow the elastomeric material to bulge between longitudinally adjacent fiber regions to provide a ribbed outer surface contour.

17. A balloon catheter, comprising:
a catheter shaft comprising a proximal end and a distal end;
a balloon comprising a generally cylindrical central body defining a length between first and second body end portions that taper to ends of the balloon attached to the distal end of the catheter shaft, the balloon expandable between a low-profile unexpanded first state and a radially-expanded second state wherein the central body defines an outer inflated diameter, wherein:
the first body end portion and second body end portion transition from the central body to the respective ends of the balloon and are substantially non-compliant such that the first body end portion and the second body end portion cannot expand longitudinally and circumferentially once the central body is inflated to the outer inflated diameter, and the central body comprises a plurality of circumferentially-constraining fibers extending circumferentially around the central body and spaced apart from one another along the length of the central body such that the central body is circumferentially substantially noncompliant, but is longitudinally compliant, the circumferentially-constraining fibers configured to allow the central body to elongate with increased volume but not substantially radially expand beyond the outer inflated diameter; and a plurality of balloon-deployable stents disposed around the central body over at least some of the circumferentially-constraining fibers, ends of adjacent stents spaced apart from one another that are deployable from the balloon in a lumen in a patient's body, wherein the circumferentially-constraining fibers comprise first elements that constrain portions of the central body from expanding beyond the outer inflated diameter and second elements under respective stents that constraint expansion of the central body to a diameter smaller than the outer inflated diameter to prevent longitudinal movement of the stents during deployment.

* * * * *